United States Patent [19]

King

[11] Patent Number: 4,478,832
[45] Date of Patent: Oct. 23, 1984

[54] PESTICIDAL O-(N-ALKOXY-SUBSTITUTED-BENZIMIDOYL)-PHOSPHORUS ESTERS AND THIOESTERS

[75] Inventor: William F. King, Novato, Calif.

[73] Assignee: Chevron Research Company, San Francisco, Calif.

[21] Appl. No.: 393,216

[22] Filed: Jun. 28, 1982

[51] Int. Cl.$^3$ .................... A01N 57/14; C07F 9/165
[52] U.S. Cl. .................................. 424/210; 260/940; 260/944; 424/211
[58] Field of Search ............... 260/944, 940; 424/210, 424/211

[56] References Cited

U.S. PATENT DOCUMENTS

| | | | |
|---|---|---|---|
| 3,760,041 | 9/1973 | Lorenz et al. | 260/944 |
| 3,872,185 | 3/1975 | Lorenz et al. | 260/944 |
| 4,054,650 | 10/1977 | Lorenz et al. | 260/944 |
| 4,076,808 | 2/1978 | Lorenz et al. | 260/944 |

*Primary Examiner*—Anton H. Sutto
*Attorney, Agent, or Firm*—S. R. LaPaglia; T. G. DeJonghe; S. L. Biggs

[57] ABSTRACT

O-(N-alkoxy-substituted-benzimidoyl)-phosphorus esters and thioesters and thioesters of the formula:

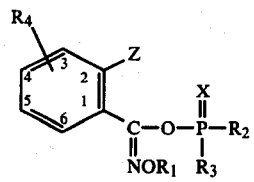

wherein X is sulfur or oxygen; $R_1$ is lower alkyl, lower alkynyl, or benzyl optionally substituted with 1 to 3 halogen atoms; $R_2$ is lower alkyl, lower alkoxy or lower alkylthio; $R_3$ is lower alkoxy, lower alkylthio, lower alkylamino or phenyl; and $R_4$ is hydrogen, cyano, trifluoromethyl, halogen, carboxyalkyl or nitro, and Z is hydrogen, cyano, trifluoromethyl, carboxyalkyl, nitro, $S(O)_n R_5$ or $SO_2 NR_6 R_7$ where n is 1 or 2, $R_5$ is lower alkyl and $R_6$ and $R_7$ are independently hydrogen or lower alkyl; provided that when $R_1$ is lower alkyl and $R_3$ is alkoxy, then $R_4$ and Z are not both hydrogen or if $R_4$ is hydrogen, Z is not nitro; and provided further that if $R_1$ is lower alkyl, $R_2$ is alkyl or alkoxy and $R_3$ is alkoxy, then if Z is hydrogen or nitro, $R_4$ is not nitro or halogen, are insecticidal.

21 Claims, No Drawings

PESTICIDAL O-(N-ALKOXY-SUBSTITUTED-BENZIMIDOYL)-PHOSPHORUS ESTERS AND THIOESTERS

BACKGROUND OF THE INVENTION

This invention relates to certain novel O-(N-alkoxy-substituted-benzimidoyl)-phosphorus esters and thioesters and their use as insecticides. These compounds are particularly effective in killing a variety of insects.

U.S. Pat. No. 3,760,041 discloses insecticidal and acaricidal compounds of the general formula:

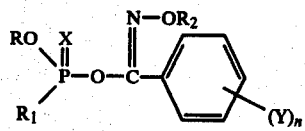

in which

R and $R_2$ each is an alkyl radical of 1 to 6 carbon atoms, $R_1$ is an alkyl or alkoxy radical of 1 to 6 carbon atoms, X is an oxygen or sulfur atom, n is an integer from 0 to 5, and Y is a halogen atom, an alkyl radical to 1 to 4 carbon atoms or a nitro group.

U.S. Pat. No. 3,872,185 discloses insecticidal and acaricidal compounds of the general formula:

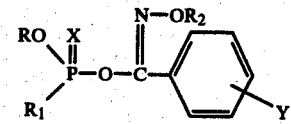

in which

R and $R_2$ each independently is alkyl of 1 to 6 carbon atoms, $R_1$ is alkyl or alkoxy of 1 to 6 carbon atoms, X is oxygen or sulfur, and Y is lower alkoxy or alkylmercapto.

U.S. Pat. No. 4,076,808 discloses insecticidal and acaricidal compounds of the general formula:

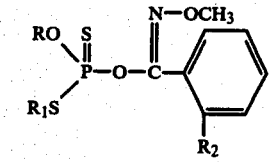

in which

R and $R_1$ each independently is alkyl with 1 to 4 carbon atoms, and $R_2$ is hydrogen or nitro.

Preferably R is ethyl and $R_1$ is alkyl with 3 or 4 carbon atoms.

U.S. Pat. No. 4,054,650 discloses a compound of the formula:

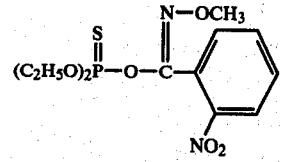

which possesses arthropodicidal properties.

U.S. Pat. No. 4,327,089 discloses a group of insecticidal and acaricidal compounds having the general formula:

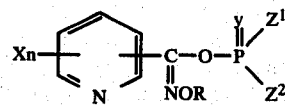

wherein X is halogen, lower alkyl, lower acyloxy, trifluoromethyl or nitro; n is 0, 1, 2 or 3, y is O or S; R is lower alkyl; and $Z^1$ and $Z^2$ each are lower alkoxy, lower alkylthio, phenyl optionally substituted with lower alkyl, phenoxy, haloalkoxy or alkylamino.

SUMMARY OF THE INVENTION

The pesticidal O-(N-alkoxy-substituted-benzimidoyl)-phosphorus esters and thioesters of this invention are represented by the formula:

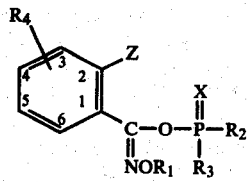

wherein X is sulfur or oxygen; $R_1$ is lower alkyl, lower alkynyl, or benzyl optionally substituted with 1 to 3 halogen atoms; $R_2$ is lower alkyl, lower alkoxy or lower alkylthio; $R_3$ is lower alkoxy, lower alkylthio, lower alkylamino or phenyl; and $R_4$ is hydrogen, cyano, trifluoromethyl, halogen, carboxyalkyl or nitro, and Z is hydrogen, cyano, trifluoromethyl, carboxyalkyl, nitro, $S(O)_n R_5$ or $SO_2 NR_6 R_7$ where n is 1 or 2, $R_5$ is lower alkyl and $R_6$ and $R_7$ are independently hydrogen or lower alkyl; provided that when $R_1$ is lower alkyl and $R_3$ is alkoxy, then $R_4$ and Z are not both hydrogen or if $R_4$ is hydrogen, Z is not nitro; and provided further that if $R_1$ is lower alkyl, $R_2$ is alkyl or alkoxy and $R_3$ is alkoxy, then if Z is hydrogen or nitro, $R_4$ is not nitro or halogen.

Among other factors, the present invention is based upon my finding that these O-(N-alkoxy-benzimidoyl) compounds exhibit surprisingly high activity as insecticides.

Representative $R_1$ groups include methyl and ethyl. Representative $R_2$ groups include ethyl, propyl, methoxy, ethoxy, methylthio and ethylthio. Representative $R_3$ groups include methoxy, ethoxy, n-propoxy, isopropoxy, ethylthio, isopropylthio, ethylamino, diethylamino, and isopropylamino. Representative $R_4$ groups include hydrogen, 3-trifluoromethyl, 4-trifluoromethyl, 4-cyano, 4-nitro, and 4-carboxymethyl. Representative Z groups include hydrogen, trifluoromethyl, cyano, and carboxymethyl.

Preferred are the compounds wherein $R_1$ is lower alkyl, $R_2$ is lower alkyl or lower alkyl, $R_3$ is lower alkoxy or lower alkylthio, one of $R_4$ or Z is hydrogen and the other is trifluoromethyl, or cyano. Preferred are those compounds where the $R_4$ substitution is at the 4-position (para-position) of the benzene ring. Especially preferred are those compounds where $R_4$ is hydrogen and Z is trifluoromethyl.

DEFINITIONS

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 3 carbon atoms and includes primary, secondary and tertiary alkyl groups. Typical lower alkyls include, for example, methyl, ethyl, n-propyl, isopropyl, and the like.

The term "alkenyl" refers to unsaturated alkyl groups having a double bond [e.g., $CH_3CH=CH-(CH_2)_2$] and includes both straight- and branched-chain alkenyl groups. "Lower alkenyl" refers to groups having a total of from 3 to 5 carbon atoms. Typical lower alkenyl groups include, for example, propenyl, but-3-enyl, pent-4-enyl, and the like.

The term "alkynyl" refers to unsaturated alkyl groups having a triple bond (e.g., $CH_3C\equiv CCH_2CH_3$) and includes both straight- and branched-chain alkynyl groups. "Lower alkynyl" refers to groups having a total of from 3 to 5 carbon atoms. Typical lower alkynyl groups include propynyl, butynyl, and the like.

The term "alkoxy" refers to the group $R'O-$ wherein $R'$ is alkyl. The term "lower alkoxy" refers to alkoxy groups having from 1 to 3 carbon atoms; examples include methoxy, ethoxy, isopropoxy, and the like.

The term "alkylthio" refers to the group $R'S-$ wherein $R'$ is alkyl. The term "lower alkylthio" refers to alkylthio groups having 1 to 3 carbon atoms; examples include methylthio, ethylthio, isopropylthio, and the like.

The term "alkylamino" refers to the group $R'R''N-$ wherein $R'$ is alkyl and $R''$ is hydrogen or alkyl. The term "lower alkylamino" refers to alkylamino groups having 1 to 6 carbon atoms. Typical alkylamino groups include methylamino, ethylamino, diethylamino, dimethylamino, and the like.

The term "alkylene" refers to the group $-(CH_2)_x-$ wherein x is an integer greater than zero, and includes, for example, methylene, ethylene, propylene and the like.

The term "carboxyalkyl" refers to the group $-CO_2R'$ where $R'$ is alkyl, preferably havng about 1 to about 6 carbon atoms. Typical carboxyalkyl groups include carboxymethyl, carboxyethyl, carboxypropyl and the like.

The terms "insecticide" and "insect" as used herein refer to their broad and commonly understood usages rather than to those creatures which, in the strict biological sense, are classified as insects. Thus, the term "insect" is used not only to include small invertebrate animals belonging to the class "Insecta", but also to other related classes of arthropods, whose members are segmented invertebrates having more or fewer than six legs such as spiders, mites, ticks, centipedes, worms, and the like.

DETAILED DESCRIPTION OF THE INVENTION

The compounds of this invention may be prepared by subjecting the appropriate N-alkoxy-benzimidoyl compounds II to a phosphorylation reaction.

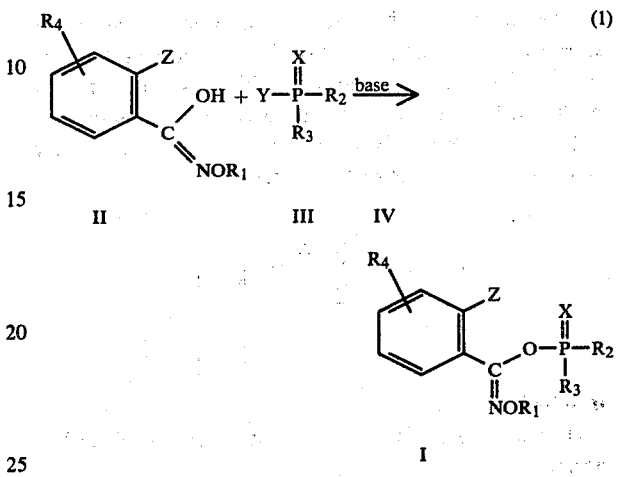

wherein X, $R_1$, $R_2$, $R_3$, $R_4$ and Z are as defined in conjunction with Formula I and Y is halogen.

The phosphorous reagents have the general formula III wherein X, $R_2$ and $R_3$ are as previously defined and Y is halogen. The phosphorylation reaction is carried out in an inert organic solvent such as methyl ethyl ketone, dimethoxyethane, acetone, acetonitrile, ether, methanol, benzene or toluene. Suitable bases IV used in the phosphorylation reaction include potassium carbonate, sodium hydride, sodium metal and the like. Although equimolar amounts of II, III and IV may be used, it is preferred to have a slight excess of III and IV which results in a better yield and easier workups of the products. Either II or III may be added to the other in the solvent; however, it is preferred to add the phosphorous reagent dissolved in a small amount of solvent to a solution of II and IV. The addition is carried out at temperatures in the range of about 0° to about 40° C. Upon completion of the addition of III, the temperature of the reaction mixture is raised, preferably to reflux (about 80° C.) and the mixture stirred (at reflux) until the reaction is complete, about 4 to about 36 hours.

At completion of the reaction, the solvent is stripped under reduced pressure and heat. The product, a liquid, is then isolated by conventional procedures such as extraction, chromatography and filtration.

The reagents, II, used in the phosphorylation reaction may be prepared according to the following reaction scheme:

Where $R_3$ is lower alkoxy or lower alkylthio:

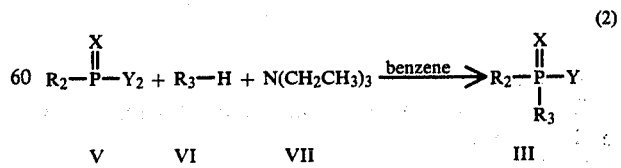

where $R_2$, $R_3$, X and Y are as defined in conjunction with reaction (1) and formula I.

Reaction (2) is carried out by adding an approximately equimolar amount of VI to a stirred solution of V in benzene. An approximately equimolar amount of VII was slowly added in a dropwise amount over a period of from about 0.5 to 1 hour. After the addition was complete, the reaction mixture was stirred for an extended period of time, about 16 hours, filtered and the solvent stripped. Other inert organic solvents such as toluene may be used in place of benzene.

Where $R_3$ is alkylamino, represented by $-NR_8R_9$, phosphorus salt III may be prepared according to the following reaction scheme:

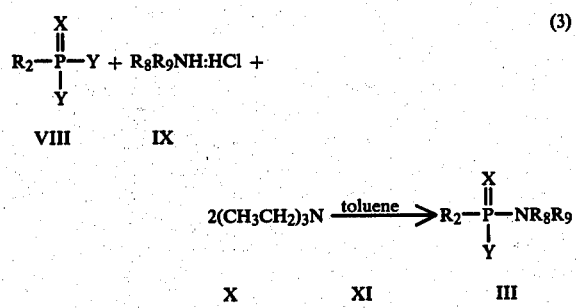

wherein X, $R_2$, $R_3$, and Y are as defined in conjunction with formula I and reaction (1), and $R_3$ is represented by $-NR_8R_9$ where $R_8$ is alkyl and $R_9$ is hydrogen or alkyl.

Reaction (3) is carried out by the addition of X to a stirred mixture of VIII and IX in XI. It is preferred that the addition be made slowly, preferably in a dropwise manner. Since the addition reaction is exothermic, it is preferred that the reaction vessel be cooled during the addition such as by use of an ice-water bath. Once the reaction is complete, the solvent is stripped. The crude product, III may then be purified by conventional procedures such as washing, extraction, and fast chromatography. Besides toluene other suitable solvents include benzene.

The N-alkoxy-benzimidoyl compound II used in the preparation of the compounds of this invention may be prepared according to the following reaction scheme:

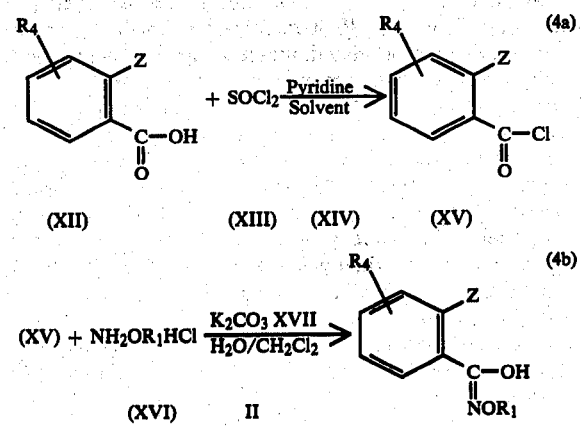

wherein $R_1$, $R_4$ and Z are as defined in conjunction with Formula I.

Reaction (4a) is carried out by warming a stirred mixture of XII in solvent to about 20° to about 35° C. with a catalytic amount of pyridine XIV (about 1 ml pyridine per 0.5 mole XII). To that mixture, a solution fo XIII in a small amount (about 10 mls) solvent is added dropwise; the resulting mixture is then refluxed for about 6 to about 36 hours. The solvent is stripped and the product XV is obtained free from XIII by chasing with toluene. Product XV is immediately dissolved in solvent and used in the second step, reaction (4b) without further isolation. Although roughly equimolar amounts of XII and XIII may be used, it is preferable to use a slight excess of XIII.

In reaction (4b), to a mixture of XVI and XVIII in methylene chloride/water, prepared at low temperature (less than $-5°$ C.) the mixture of XV in solvent is added and the resulting mixture stirred for about 6 to about 36 hours. Although roughly equimolar amounts of XV and XVI may be used, it is preferable to use a slight excess of XVI.

Reactions (4a) and (4b) are carried out in an inert organic solvent; suitable solvents include, methylene chloride, ether and toluene.

The product II, a solid, may be isolated by conventional procedures such as stripping, extraction, chromatography, filtration and crystallization.

Alternatively, where the acid chloride XV is commercially available, the N-alkoxy-benzimidoyl intermediate II may be prepared using the acid chloride XV according to the following reaction scheme:

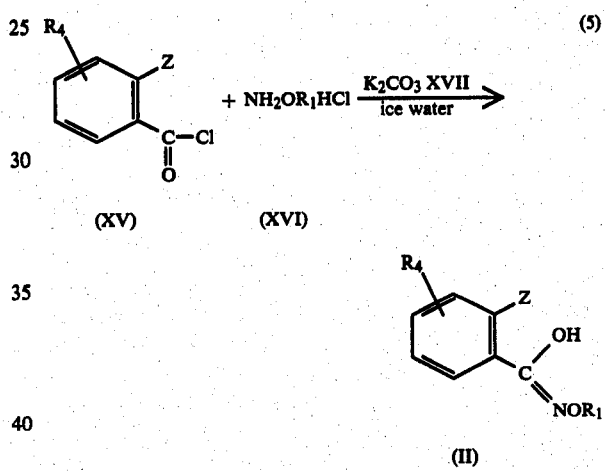

wherein $R_1$, $R_4$ and Z are as defined in conjunction with Formula I.

Reaction (5) is carried out by adding XV to a stirred mixture of XVI and XVII in ice water dropwise. The resulting mixture is then stirred for about 4 to about 16 hours at room temperature. The product II a solid may then be isolated by conventional procedures such as stripping, extraction, chromatography, filtration, crystallization and the like. Although roughly equimolar amounts of XV and XVI may be used, it is preferable to use a slight excess of XVI.

UTILITY

The compounds of this invention are surprisingly effective in killing a variety of insects.

The present compounds can be stored and applied as formulations incorporated with compatible biologically inert extenders or carriers such as are typically employed for facilitating dispersion of active ingredients for agricultural chemical applications. These formulations typically contain about from 0.5 to 95 weight % of the present compound, and optionally can contain compatible insecticides, fungicides, etc., and the remainder biologically inert material including dispersing agents, emulsifying agents, wetting agents and carriers.

Such formulations can be formulated as sprays, dusts, or granules and applied to the insects and/or their environment or hosts susceptible to insect attack. They can be formulated as granules of large particle size, as powdery dusts, as wettable powders, as emusifiable concentrates, as solutions, or as any of several other known types of formulations, depending on the desired mode of application. (Wettable powders generally refer to a form of finely divided particles which disperse readily in water or other dispersant.) Typical carriers include fuller's earth, kaolin clays, silicas, and other highly absorbent, readily wet, inorganic diluents. Typical wetting, dispersing, or emulsifying agents used in agricultural formulations include, for example, the alkyl and alkylaryl sulfonates and sulfonates and their sodium salts; alkylamide sulfonates, including fatty methane taurides, alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long chain mercaptans and ethylene oxide. Many other types of useful surface active agents are available in commerce. The surface active agent, when used, normally comprises from one percent to fifteen percent by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about fifty microns. A typical dust formulation useful herein contains about 65–80 weight % silica and 35–20 weight % of the compound(s) of the invention.

Useful liquid concentrates include the emulsifiable concentrates, which are homogeneous liquid or paste compositions which are readily dispersed in water to other dispersant, and can consist entirely of the compound(s) of the invention with a liquid or solid emulsifying agent, or can also contain a liquid carrier, such as xylene, heavy aromatic naphthas, isophorone, and other non-volatile organic solvents. These concentrates are usually dispersed in water, or their liquid carrier, and then applied as a spray or paint to the area to be treated.

Other useful formulations include simple solutions of the active compound in a dispersant in which it is completely soluble at the desired concentration, such as acetone, alkylated naphthalenes, xylenes, or other organic solvents.

Optimum formulation concentrations and the manner and frequency of application may vary somewhat with the particular species of insect, the degree of infestation, the environment, including type of soil, soil conditions and weather conditions (e.g., rain fall), and can be obtained by routine experimentation.

A further understanding of my invention can be had from the following non-limiting examples.

EXAMPLE 1

Preparation of N-methoxy-2-trifluoromethylbenzhydroxamic acid

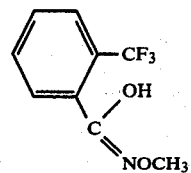

To a stirred solution of 25 g (0.30 mole) methoxyamine hydrochloride ($NH_2OCH_3 \cdot HCl$) and 43 g (0.31 mole) potassium carbonate in about 200 mls ice water, 50 g (0.259 mole) of 2-trifluoromethyl-benzoylchloride were added at a slow to moderate dropping rate. The reaction mixture was stirred overnight. The mixture was suction-filtered and the residue, the crude product, was dried in a vacuum oven. The crude product was then washed with hexane (about 100 mls) and diethylether (about 2 to 3 mls), as an extra purifying step, to give the product a white solid, melting point 101° to 103° C.

Elemental analysis for $C_9H_8F_3NO_2$ showed: calculated %C 49.3, %H 4.14, and %N 6.39; found %C 49.56, %H 3.68, and %N 6.49.

EXAMPLE 2

Preparation of N-methoxy-4-cyanobenzhydroxamic acid

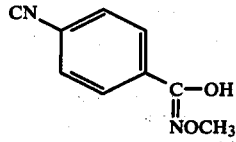

A mixture of 29.4 g (0.350 mole) methoxyaminehydrochloride and 50 g (0.36 mole) potassium carbonate in about 200 mls was stirred, maintaining the temperature below −5° C. until the reactants were dissolved. To that solution, 50 g (0.302 mole) 4-cyano-benzoylchloride were dropped in slowly, maintaining the temperature of the reaction mixture below 0° C. during the addition. The reaction mixture was stirred overnight. The reaction mixture was suction-filtered. The residue, containing the crude product was dried in a heated vacuum oven and then washed with hexane (about 100 mls) and ether (about 2–3 mls) to give the product an off-white solid.

Elemental analysis for $C_9H_8N_2O_2$ showed: calculated %C 61.4, %H 4.58, and %N 15.9; found %C 55.4, %H 3.78, and %N 14.1.

EXAMPLE 3

Preparation of Ethyl-O-isopropylphosphonothioic chloride

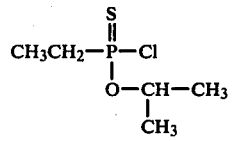

To a stirred mixture of 74.2 g (0.455 mole)

ethylphosphonothioic acid dichloride in 400 mls benzene, 30.1 g (0.5 mole) isopropyl alcohol was added. To that mixture 50.6 g (0.5 mole) triethylamine was added at a dropwise rate overnight. The mixture was then warmed for about 1 hour. The mixture was filtered by gravity. Most of the solvent (benzene) was stripped off under reduced pressure and heat to give ethyl-O-isopropylphosphonothioic chloride

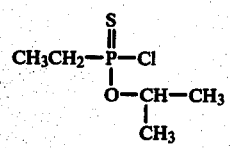

EXAMPLE 4

Preparation of Ethyl-N,N-diethylaminophosphonic chloride

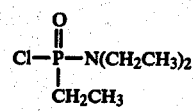

In a one-liter flask, 73.5 g (0.5 mole) of ethylphosphonic dichloride

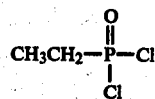

are dissolved in 300 mls toluene. To that mixture 57 g (0.52 mole), diethylamine hydrochloride [(CH$_2$CH$_3$)$_2$NH.HCl] is added with stirring. To the resulting stirred mixture, 105 g triethylamine is added in a dropwise manner. During the addition, the temperature of the reaction mixture is controlled by the use of an ice-water bath. The reaction mixture is allowed to come to room temperature, and stirred for 14 hours.

After the reaction is complete, the toluene is stripped under reduced pressure. Dichloromethane (about 300 mls) and water (about 150 mls) are added to the residue (crude product) and the mixture is stirred. The phases ae separated, the product is extracted in the dichloromethane layer, and the aqueous layer is discarded. The dichloromethane layer is dried with magnesium sulfate and then filtered. The dichloromethane is then stripped to give the product.

EXAMPLE 5

Preparation of
Ethyl-N,N-diethylaminophosphonothioic chloride

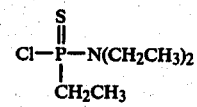

In a one-liter flask, 81.5 g (0.5 mole) of ethylphosphonothioic dichloride

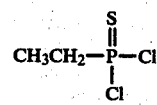

were dissolved in 300 mls toluene. To that mixture, 57 g (0.52 mole) diethylamine hydrochloride [(CH$_3$CH$_2$)$_2$NH.HCl] was added with stirring. To the resulting stirred mixture, 105 g triethylamine was then added dropwise. During the addition, the temperature of the reaction mixture was controlled by use of an ice-water bath. The reaction mixture was allowed to come to room temperature, and stirred 14 hours.

The toluene was stripped using reduced pressure. Dichloromethane (about 300 mls) and water (about 150 mls) were added to the residue (crude product) and the mixture was stirred. The phases were separated, the product extracted in the dichloromethane (organic) phase, and the aqueous phase was discarded. The dichloromethane phase was dried with magnesium sulfate, and then filtered. The dichloromethane was then stripped to give about 90 g of product.

EXAMPLE 6

Preparation of
O,O-diethyl-O-(N-methoxy-2-trifluoromethylbenzimidoyl)thionophosphate

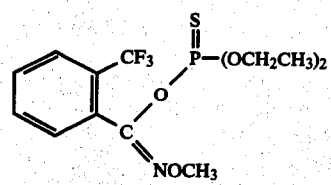

A mixture of 3.3 g (0.015 mole) of N-methoxy-2-trifluoromethylbenzhydroxamic acid

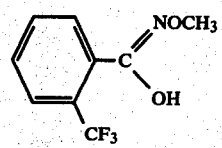

the product of Example 1 and 2.4 g (0.017 mole) of K$_2$CO$_3$ (potassium carbonate) in about 60 mls methyl ethyl ketone was stirred together and heated to about 40° C. for one half hour. To that mixture 3.2 g (0.017 mole) of diethylchlorothiophosphate

in a small amount (about 5 mls) of methyl ethyl ketone was added. The resulting mixture was then refluxed several about 6 hours.

The methylethyl ketone was removed under reduced pressure and heat, to give the crude product. Water (about 75 mls) and methylene chloride (about 75 mls) were added to the crude product and the mixture stirred. The aqueous and methylene chloride phases were separated, the product separating with the methylene chloride layer. The methylene chloride layer was dried over magnesium sulfate, filtered and the methylene chloride stripped. Chromatography on a silica-gel column, eluting with hexane:methylene chloride 3:1 gave about 4.7 g of the product, a colorless liquid.

Elemental analysis for $C_{13}H_{17}F_3NO_4PS$ showed: calculated %C 42.1, %H 4.62 and %N 3.77; found %C 41.6, %H 4.82, and %N 3.98.

EXAMPLE 7

Preparation of
O-ethyl-O(N-methoxy-2-trifluoromethylbenzimidoyl)-ethanethionophosphonate

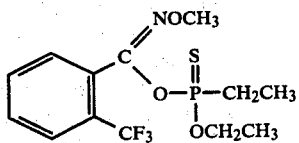

A mixture of 4.4 g (0.02 mole) of the product of Example 1 and 3.5 g (0.025 mole) potassium carbonate in about 75 mls methyl ethyl ketone was stirred together with gentle heat for about an hour. To the resulting mixture, 3.5 g (0.02 mole) ethyl-O-ethylphosphonothioic chloride

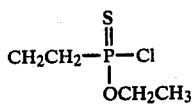

in a small amount (about 5 mls) methyl ethylketone was added dropwise. The reaction mixture was refluxed for about 8 hours. The solvent was stripped under reduced pressure and heat. Water (about 75 mls) and methylene chloride (about 75 mls) was added to the residue and the resulting mixture was stirred. The phases were separated; the organic (methylene chloride) layer extracting the product. The methylene chloride layer was dried over magnesium sulfate and filtered. Stripping of the solvent followed by chromatography on a silica gel column, eluting with hexane:methylene chloride 4:1 gave about 2.6 g of the product, a clear amber liquid.

Elemental analysis for $C_{13}H_{17}F_3NO_3PS$ showed: calculated %C 43.9, %H 4.82, and %N 3.94; found %C 44.5, %H 4.75, and %N 4.24.

EXAMPLE 8

Preparation of
O,O-dimethyl-O-(N-methoxy-2-trifluoromethylbenzimidoyl)thionophosphate

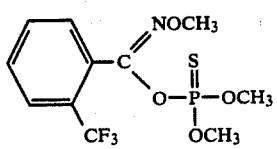

A mixture of 6.6 g (0.03 mole) of the product of Example 1 and 1.7 g of 50% sodium hydride (0.035 mole) in about 75 mls dimethoxyethane were stirred together under gentle heat for about one half-hour. To that mixture 4.7 g (0.29 mole) in a small amount (about 5 mls) solvent was added at a moderate dropping rate. After the addition was complete, the reaction mixture was refluxed for about 8 hours. The solvent was removed under reduced pressure and heat. Water (about 75 mls) and methylene chloride (about 75 mls) were added to the residue and the resulting mixture was stirred. The phases were separated, the methylene chloride (organic) phase extracting the product. The methylene chloride layer was dried over magnesium sulfate and filtered. Stripping of the methylene chloride, followed by chromatography on a silica gel column eluting with hexane:methylene chloride 4:1, gave about 2.7 g of the product, a colorless liquid.

Elemental analysis for $C_{11}H_{13}F_3NO_4PS$ showed: calculated %C 38.5, %H 3.82, and %N 4.08; found %C 38.23, %H 4.18, and %N 3.47.

EXAMPLE 9

Preparation of
S-isopropyl-O-(N-methoxy-4-nitrobenzimidoyl)ethanethionophosphonate

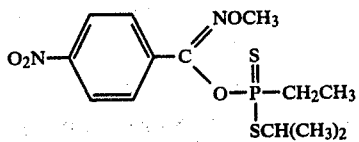

A mixture of 3 g (0.0153 mole)

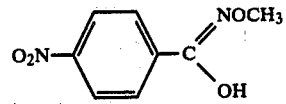

N-methoxy-4-nitrobenzhydroxamic acid and 2.1 g potassium carbonate in about 75 mls acetonitrile was stirred together with gentle warming (to about 40° C.) for about one-half hour. To that mixture 3.1 g (0.0152 mole) of ethyl-S-isopropylphosphonothioic chloride in a small amount (about 5 mls) methyl ethyl ketone was added at a moderate drop rate. The reaction mixture was refluxed about 6 hours, warmed for about 48 hours and then refluxed about 2 hours.

After the reaction mixture was allowed to cool, the acetonitrile was removed under reduced pressure and heat. Water (about 75 mls) and methylene chloride (about 75 mls) were added to the residue and the resulting mixture stirred. The aqueous and organic (methylene chloride) phases were separated, the product separating with the methylene chloride layer. The methylene chloride layer was then washed with water (about 35 mls), dried with magnesium sulfate, filtered and the methylene chloride stripped. Upon sitting, the product solidified. The product had a melting point of 63°-64° C.

Elemental analysis for $C_{13}H_{19}N_2O_4PS_2$ showed: calculted % C 43.1, % H 5.28, and % N 7.73; found % C 44.24, % H 5.53, and % N 8.02.

Compounds made in a manner consistent with Examples 1 to 9 are found in Table I.

EXAMPLE A-Aphid Control

Compounds of this invention were tested for their insecticidal activity against cotton aphids (*Aphis gossypii* Glover). An acetone solution of the test compound containing a small amount of non-ionic emulsifier was diluted with water to give a concentration of 40 ppm.

Cucumber leaves infested with cotton aphids were dipped in the test compound solution. Mortality readings were taken after 24 hours. The results expressed as % control, are tabulated in Table II.

EXAMPLE B-MITE CONTROL

Compounds of this invention were tested for their insecticidal ability against two-spotted mites (*Tetranychus urticae*). An acetone solution of the test compound containing a small amount of non-ionic emulsifier was diluted with water to give a concentration of 40 ppm. Lima bean leaves which were infested with mites were dipped in the test compound solution. Mortality readings were taken after 24 hours. The results, expressed as % control, are tabulated in Table II.

EXAMPLE C-MITE EGG CONTROL

Compounds of this invention were tested for their ovicidal activity against eggs of the two-spotted spider mite (*Tetranychus urticae*). An acetone solution of the test toxicant containing a small amount of non-ionic emulsifier was diluted with water to give a concentration of 40 ppm. Two days before testing, 2-week old lima bean plants were infested with spider mites. Two days after infestation, leaves from the infested plants are dipped in the toxicant solution, placed in a petridish with filter paper and allowed to dry in the open dish at room temperature. The treated leaves were then held in covered dishes at about 31° to 33° C. for seven days. On the eighth day egg mortality readings are taken. The results, expressed as % control, are tabulated in Table II.

EXAMPLE D-HOUSEFLY

Compounds of this invention were tested for their insecticidal activity against the housefly (*Musca domestica L.*). A 500 ppm acetone solution of the test compound was placed in a microsprayer (atomizer). A random mixture of anesthetized male and female flies was placed in a container and 55 mg of the above-described acetone solution was sprayed on them. A lid was placed on the container. A mortality reading was then taken after 24 hours. The results are expressed as % control and are reported in Table II.

EXAMPLE E-AMERICAN COCKROACH

Compounds of this invention were tested for their insecticidal activity against the American cockroach (*Periplaneta americana L.*). A 500 ppm acetone solution of the test compound was placed in a microsprayer (atomizer). A random mixture of anesthetized male and female roaches was placed in a container and 55 mg of the above-described solution was sprayed on them. A lid was placed on the container. A mortality reading was made after 24 hours. The results, expressed as % control, are reported in Table II.

EXAMPLE F-ALFALFA WEEVIL

Compounds of this invention were tested for their insecticidal activity against the alfalfa weevil (*H. Brunneipennis Boheman*). A 500 ppm acetone solution of the test compound was placed in a microsprayer (atomizer). A random mixture of male and female weevils was placed in a container and 55 mg of the above-described acetone solution was sprayed on them. A lid was placed on the container. A mortality reading was made after 24 hours. The results are expressed as % control and are tabulated in Table II.

EXAMPLE G-CABBAGE LOOPER

Compounds of this invention were tested for their insecticidal activity against cabbage looper (*Trichoplusia ni*). An acetone solution of the test compound containing a small amount of non-ionic emulsifier was diluted with water to give a concentration of 500 ppm. Excised cucumber leaves were dipped in the test compound solution and allowed to dry. The leaves were then infested with cabbage looper larvae. Mortality readings were taken after 24 hours. The results are expressed as % control and are reported in Table II.

EXAMPLE H-CONTROL OF MOSQUITO LARVAE

The compounds of this invention were tested for control of mosquito larvae (*Aedes aegypti*). A plastic cup was filled with 90 ml deionized water and then infested with early 4th-stage mosquito larvae contained in 10 ml water. One rabbit food pellet was added to the cup to provide food for the larvae. A 200 microliter aliquot of a 500 ppm solution of the test compound was added to the cup. The water was then thoroughly mixed to give a final concentration of test compound of 0.1 ppm. The cup was covered with a plastic lid in order to prevent evaporation and to confine any subsequently emerging adult mosquitos. The cup was kept at 27° C. for 6 days at which time mortality readings were taken. The results, expressed as % control, are reported in Table II.

TABLE I

Compounds of the Formula:

$$\text{benzene ring with } R_4 \text{ substituent, } Z, \text{ and } C(=N-OR_1)-O-P(=X)(R_2)(R_3)$$

| Compound No. | X | $R_1$ | $R_2$ | $R_3$ | $R_4$ | Z | Physical State | % Carbon Calc. | % Carbon Fd. | % Hydrogen Calc. | % Hydrogen Fd. | % Nitrogen Calc. | % Nitrogen Fd. |
|---|---|---|---|---|---|---|---|---|---|---|---|---|---|
| 1 | S | $CH_3$ | $OCH_2CH_3$ | $OCH_2CH_3$ | 3-$CF_3$ | H | clear liquid | 42.1 | 41.3 | 4.62 | 4.79 | 3.77 | 3.21 |
| 2 | S | $CH_3$ | $OCH_3$ | $OCH_3$ | 3-$CF_3$ | H | light yellow liquid | 38.5 | 38.9 | 3.82 | 3.87 | 4.1 | 4.15 |
| 3 | S | $CH_3$ | $OCH_3$ | $OCH_3$ | 4-CN | H | light yellow liquid | 43.9 | 46.3 | 4.36 | 4.59 | 9.33 | 8.78 |

TABLE I-continued

Compounds of the Formula:

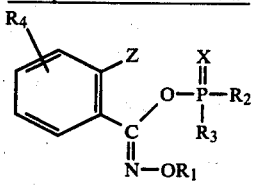

| Compound No. | X | $R_1$ | $R_2$ | $R_3$ | $R_4$ | Z | Physical State | % Carbon Calc. | % Carbon Fd. | % Hydrogen Calc. | % Hydrogen Fd. | % Nitrogen Calc. | % Nitrogen Fd. |
|---|---|---|---|---|---|---|---|---|---|---|---|---|---|
| 4 | S | $CH_3$ | $OCH_3$ | $OCH_3$ | H | $CF_3$ | colorless liquid | 38.5 | 38.2 | 3.82 | 4.18 | 4.08 | 3.47 |
| 5 | S | $CH_3$ | $OCH_3$ | $OCH_3$ | 4-$CF_3$ | | yellow liquid | 38.5 | 39.57 | 3.82 | 3.80 | 4.086 | 4.3 |
| 6 | S | $CH_3$ | $OCH_2CH_3$ | $OCH_2CH_3$ | 4-CN | H | rose semi-liquid | 47.6 | 45.1 | 5.22 | 5.17 | 8.53 | 7.59 |
| 7 | S | $CH_3$ | $OCH_2CH_3$ | $OCH_2CH_3$ | H | $CF_3$ | colorless liquid | 42.1 | 41.6 | 4.62 | 4.82 | 3.77 | 3.98 |
| 8 | S | $CH_3$ | $OCH_2CH_3$ | $OCH_2CH_3$ | 4-$CF_3$ | H | colorless liquid | 42.1 | 42.5 | 4.62 | 4.81 | 3.77 | 3.79 |
| 9 | S | $CH_3$ | $CH_2CH_3$ | $SCH(CH_3)_2$ | 4-$NO_2$ | H | light yellow liquid | 43.1 | 44.2 | 5.28 | 5.53 | 7.73 | 8.02 |
| 10 | S | $CH_3$ | $CH_2CH_3$ | $SCH(CH_3)_2$ | H | $CF_3$ | colorless liquid | 43.6 | 44.4 | 4.96 | 5.3 | 3.63 | 3.73 |
| 11 | S | $CH_3$ | $CH_2CH_3$ | $SCH(CH_3)_2$ | 3-$CF_3$ | H | clear liquid | 43.6 | 43.9 | 4.97 | 5.21 | 3.63 | 3.59 |
| 12 | S | $CH_3$ | $CH_2CH_3$ | $SCH(CH_3)_2$ | 4-CN | H | colorless liquid | 49.1 | 48.1 | 5.59 | 5.94 | 8.18 | 7.64 |
| 13 | S | $CH_2CH_3$ | $OCH_2CH_3$ | $OCH_2CH_3$ | H | $CF_3$ | clear liquid | 46.9 | 46.3 | 5.52 | 5.52 | 3.65 | 3.54 |
| 14 | S | $CH_2CH_3$ | $OCH_2CH_3$ | $OCH_2CH_3$ | H | $CF_3$ | clear liquid | 43.6 | 43.3 | 4.97 | 5.13 | 3.64 | 3.48 |
| 15 | S | $CH_3$ | $CH_3$ | $OCH(CH_3)_2$ | H | $CF_3$ | clear liquid | 43.9 | 42.9 | 4.82 | 3.96 | 3.94 | 3.96 |
| 16 | S | $CH_2CH_3$ | $OCH_3$ | $OCH_3$ | H | $CF_3$ | clear liquid | 40.3 | 42.2 | 4.23 | 4.51 | 3.92 | 4.14 |
| 17 | S | $CH_2CH_3$ | $CH_2CH_3$ | $OCH_2CH_3$ | H | $CF_3$ | clear liquid | 46.9 | 46.1 | 5.52 | 5.72 | 3.65 | 3.36 |
| 18 | O | $CH_3$ | $OCH_2CH_3$ | $OCH_2CH_3$ | H | $CF_3$ | clear liquid | 43.9 | 45.8 | 4.83 | 4.89 | 3.94 | 4.6 |
| 19 | S | $CH_2CH_3$ | $CH_2CH_3$ | $SCH(CH_3)_2$ | H | $CF_3$ | clear liquid | 45.1 | 44.1 | 8.29 | 5.99 | 3.51 | 3.13 |
| 20 | S | $CH_3$ | $CH_2CH_3$ | $OCH_2CH_3$ | H | $CF_3$ | clear amber liquid | 43.9 | 44.5 | 4.82 | 4.75 | 3.92 | 4.24 |
| 21 | S | $CH_3$ | $CH_3$ | $OCH_2CH_3$ | H | $CF_3$ | amber liquid | 42.2 | 41.4 | 4.43 | 4.28 | 4.1 | 4.1 |
| 22 | S | $CH_3$ | $OCH_2CH_3$ | $NHCH(CH_3)_2$ | H | $NO_2$ | amber liquid | 43.2 | 40.4 | 5.58 | 5.73 | 11.6 | 10.3 |

TABLE II

Insecticidal Activity

| Compound No. | Aphid | Mite Adult | Mite Egg | Housefly | Am. Roach | Alfalfa Weevil | Cabbage Looper | Mosquito Larvae |
|---|---|---|---|---|---|---|---|---|
| 1 | 0 | 0 | 0 | 95 | 93 | 20 | 0 | 0 |
| 2 | 0 | 0 | 0 | — | 100 | 10 | 0 | — |
| 3 | 100 | 75 | 40 | 100 | 100 | 70 | 0 | 100 |
| 4 | 100 | 25 | 0 | 100 | 100 | 90 | 100 | 100 |
| 5 | 25 | 0 | 0 | 100 | 60 | 0 | 0 | 0 |
| 6 | 100 | 0 | 20 | 100 | 100 | — | 50 | 100 |
| 7 | 51 | 70 | 0 | 100 | 100 | 100 | 100 | 100 |
| 8 | 5 | 20 | 0 | 100 | 70 | 60 | 0 | 70 |
| 9 | 100 | 65 | 30 | 0 | 0 | 0 | 0 | 0 |
| 10 | 70 | 94 | 29 | 90 | 0 | 0 | 0 | 0 |
| 11 | 60 | 80 | 0 | — | 0 | 90 | 20 | — |
| 12 | 100 | 30 | 30 | 0 | 0 | — | 30 | 100 |
| 13 | 0 | 0 | 0 | 99 | 35 | 0 | 60 | — |
| 14 | 0 | 45 | 0 | 100 | 100 | 0 | 100 | 100 |
| 15 | 15 | 80 | 0 | 100 | 95 | 20 | 100 | 0 |
| 16 | 10 | 0 | 0 | 100 | 100 | 20 | 90 | 100 |
| 17 | 10 | 10 | — | 100 | 0 | 20 | 0 | — |
| 18 | 100 | 0 | 0 | 0 | 100 | 60 | 100 | 100 |
| 19 | 55 | 80 | 0 | 70 | 0 | — | 0 | 0 |
| 20 | 97 | 90 | 0 | 100 | 100 | — | 100 | — |
| 21 | 100 | 75 | 0 | 100 | 100 | 10 | 100 | 100 |
| 22 | 60 | 0 | 30 | 0 | 30 | 10 | 0 | 70 |

What is claimed is:
1. A compound of the formula:

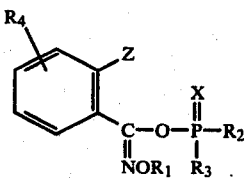

wherein X is sulfur or oxygen; $R_1$ is lower alkyl; $R_2$ is lower alkyl or lower alkoxy; $R_3$ is lower alkoxy or lower alkylthio; and one of $R_4$ or Z is hydrogen and the other is trifluoromethyl or cyano.

2. A compound according to claim 1 wherein $R_4$ is at the 4-position of the ring.

3. The compound according to claim 2 wherein X is sulfur, $R_1$ is methyl, $R_2$ is methoxy $R_3$, is methoxy, $R_4$ is cyano and Z is hydrogen.

4. A compound according to claim 2 wherein $R_4$ is hydrogen and Z is trifluoromethyl.

5. A compound according to claim 4 wherein X is sulfur, $R_1$ is methyl, $R_2$ is methoxy, and $R_3$ is methoxy.

6. A compound according to claim 4 wherein X is sulfur, $R_1$ is methyl, $R_2$ is ethyl and $R_3$ is ethoxy.

7. A compound according to claim 4 wherein X is sulfur, $R_1$ is methyl, $R_2$ is methyl and $R_3$ is ethoxy.

8. A method of killing insects which comprises contacting said insect or its environment with an insecticidally effective amount of a compound of claim 1.

9. A method of killing insects which comprises contacting said insect or its environment with an insecticidally effective amount of a compound of claim 2.

10. A method of killing insects which comprises contacting said insect or its environment with an insecticidally effective amount of a compound of claim 3.

11. A method of killing insects which comprises contacting said insect or its environment with an insecticidally effective amount of a compound of claim 4.

12. A method of killing insects which comprises contacting said insect or its environment with an insecticidally effective amount of a compound of claim 5.

13. A method of killing insects which comprises contacting said insect or its environment with an insecticidally effective amount of a compound of claim 6.

14. A method of killing insects which comprises contacting said insect or its environment with an insecticidally effective amount of a compound of claim 7.

15. A composition for killing insects comprising a biologically inert carrier and an insecticidally effective amount of a compound of claim 1.

16. A composition for killing insects comprising a biologically inert carrier and an insecticidally effective amount of a compound of claim 2.

17. A composition for killing insects comprising a biologically inert carrier and an insecticidally effective amount of a compound of claim 3.

18. A composition for killing insects comprising a biologically inert carrier and an insecticidally effective amount of a compound of claim 4.

19. A composition for killing insects comprising a biologically inert carrier and an insecticidally effective amount of a compound of claim 5.

20. A composition for killing insects comprising a biologically inert carrier and an insecticidally effective amount of a compound of claim 6.

21. A composition for killing insects comprising a biologically inert carrier and an insecticidally effective amount of a compound of claim 7.

* * * * *